United States Patent [19]
Olsson et al.

[11] Patent Number: 5,615,669
[45] Date of Patent: Apr. 1, 1997

[54] GAS MIXTURE AND DEVICE FOR DELIVERING THE GAS MIXTURE TO THE LUNGS OF A RESPIRATORY SUBJECT

[75] Inventors: Sven-Gunnar Olsson, Arloev; Goeran Rydgren, Bunkeflostrand; Anders Larsson, Kaevlinge; Stefan Brauer, Södra Sandby; Anders Linge, Kaevlinge, all of Sweden

[73] Assignee: Siemens Elema AB, Solna, Sweden

[21] Appl. No.: 570,525

[22] Filed: Dec. 11, 1995

Related U.S. Application Data

[62] Division of Ser. No. 279,108, Jul. 22, 1994.

[51] Int. Cl.$^6$ ................................................. A61M 15/00
[52] U.S. Cl. ........................ 128/203.12; 128/203.14; 128/203.25
[58] Field of Search ...................... 128/203.12, 203.14, 128/203.25

[56] References Cited

U.S. PATENT DOCUMENTS 4,547,316 10/1985 Yamauchi ............................... 252/571
4,905,685 3/1990 Olsson et al. ......................... 128/203.12
5,099,834 3/1992 Fishman ............................... 128/203.12

FOREIGN PATENT DOCUMENTS 0496336   7/1992   European Pat. Off. .
0570612   11/1993  European Pat. Off. .
WO92/10228 6/1992   WIPO .
WO92/11887 7/1992   WIPO .

*Primary Examiner*—Aaron J. Lewis
*Attorney, Agent, or Firm*—Hill, Steadman & Simpson

[57] ABSTRACT

In conjunction with the diagnosis of conditions in and treatment of the lungs, a small amount of NO is supplied to the lungs in some cases. A gas mixture for this purpose is disclosed in which an inert, non-toxic trace gas is present in an exact concentration in relation to NO, in order to simply and safely control the amount of NO then supplied to the lungs. The amount of NO supplied can be determined by determining the concentration of the trace gas. A method and device for administering breathing gas to a patient together with the aforementioned gas mixture are also disclosed.

7 Claims, 1 Drawing Sheet

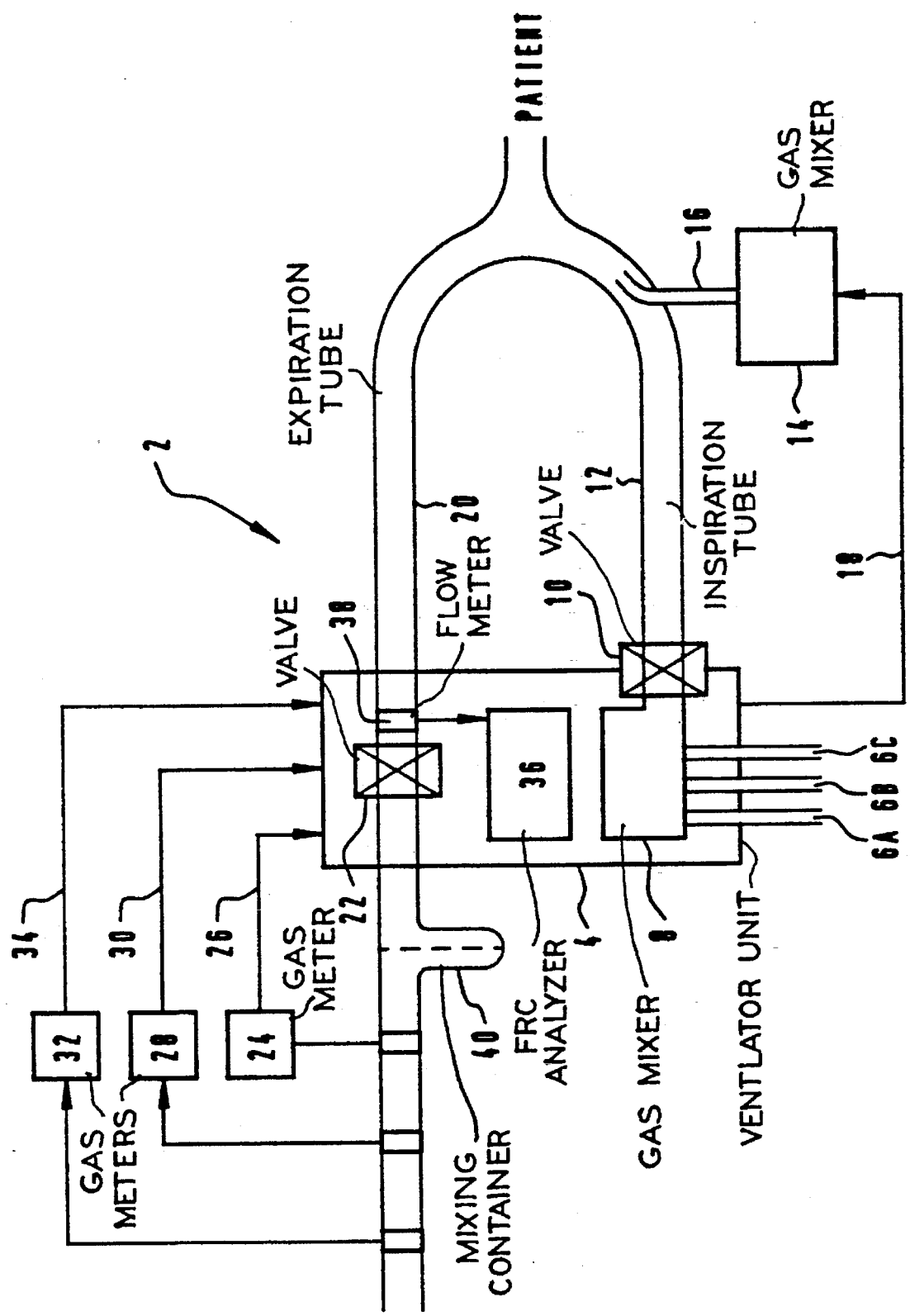

GAS MIXTURE AND DEVICE FOR DELIVERING THE GAS MIXTURE TO THE LUNGS OF A RESPIRATORY SUBJECT

This is a division of application Ser. No. 08/279,108, filed Jul. 22, 1994, pending.

BACKGROUND OF THE INVENTION

1. Field of the Invention

The present invention relates to a gas mixture intended for delivery, together with a breathing gas, to the lungs of a living being, said gas mixture containing a pre-defined concentration of NO.

2. Description of the Prior Art

All exchanges between blood gases and the atmosphere take place in the lungs, more particularly in the pulmonary alveoli. When the lungs are defective or diseased, the pulmonary alveoli may be afflicted by dysfunction which impairs or prevents the exchange of gas between the blood and the atmosphere. This is also true in the case of defects or disease affecting blood vessels in the lungs. Resistance to the flow of blood through the lungs could then increase, thereby increasing the load on the heart. Very small amounts of nitric oxide (NO) can be supplied to the lungs in order to diagnose pulmonary function and treat the lungs. Nitric oxide relaxes smooth muscle cells in blood vessels and bronchi. Relaxation of the vascular musculature increases the flow of blood through the vessels, thereby improving the exchange of gas between the blood and the atmosphere and reducing the load on the heart. Resistance to flow through the lungs can be determined by measuring the pressure in the pulmonary artery. As a result, the effect of NO administration can be directly measured. If no effect is measurable, the capillaries are either already fully dilated or heavily calcified. Relaxation of smooth muscle cells in the bronchi counteracts bronchospasm and asthma. Nitric oxide gas also diffuses through the lung membrane and can be absorbed by the blood in unlimited quantities, in principle, thereby making it possible to measure the diffusion capacity of the lungs by determining the amount of diffused nitric oxide. NO can also be used in different types of respiratory treatment of adults and children and in the monitoring of respiratory treatment and other diagnostic measures.

In WO 92/10288 the use and effects of NO are described in detail. The document also describes how NO in a mixture of $H_2$ and $O_2$ can be delivered to a patient's lung with a ventilator.

European Application 0 570 612 describes a device for delivering very small gas flows to a patient. An accurate concentration of, e.g., NO can be supplied to a patient's lungs with a very small flow of gas.

Since the amounts of nitric oxide supplied are very small, i.e., generally from one or two ppm up to about 100 ppm, measuring the concentration of nitric oxide supplied to a patient's lungs is difficult. The calculations are especially complicated by the circumstance that known NO meters are sensitive to pressure variations, as occur on the inspiratory side of a ventilator system, in principle, there are four types of meters: a chemoluminance meter which records energy quanta emitted in the chemical reaction $NO \rightarrow NO_2 \rightarrow NO$, mass spectrometers, infrared absorption meters and chemical cells which register electron emissions in the reaction $NO \rightarrow NO_2$. In order to measure NO concentrations, the known NO meters also need large, continuous flows of breathing gas. Diverting a large flow from the inspiratory flow before it reaches the patient also complicates flow control.

NO is also a highly reactive gas which chemically reacts with oxygen, $O_2$, to form nitrogen dioxide, $NO_2$, a toxic gas. As a rule, relatively large amounts of $O_2$ are supplied in treatment with NO. To prevent NO from reacting with $O_2$ before it reaches the lungs, NO must be added to the breathing gas (e.g. air and $O_2$) at a location close to the patient. This also presents major problems in the measurement of the NO concentration because the gas meter must be placed between the lungs and point at which NO is added. This distance must be as short as possible in order to minimize the amount of $NO_2$ reaching the lungs, but the amount of NO gas supplied must have time to mix with the breathing gas before the NO concentration is measured. In other words, gas meters will be unable to supply a reliable reading of the NO concentration if NO is added to the breathing gas very close to the patient so as to minimize the formation of $NO_2$. If NO is added to the breathing gas at a greater distance in order to permit correct measurement of the NO concentration, more $NO_2$ will form. $NO_2$ molecules can be filtered out in an absorber arranged before the patient, but the concentration of NO could fall below the desired level if numerous $NO_2$ molecules are formed. Moreover, as noted above, most modern NO meters require a relatively large, continuous flow of gas past the meter. Any diversion of gases from the patient would give NO time to form more $NO_2$ molecules before the gas reaches the patient's lungs. NO is generally supplied diluted in $N_2$, primarily to control the small amounts of NO to be supplied.

SUMMARY OF THE INVENTION

One object of the invention is to provide a gas mixture containing a predetermined concentration of NO so the amount of NO supplied to a patient can be simply and exactly determined.

Another object of the invention is to provide a method and device for delivering a predetermined amount of NO to the lungs.

The above-described problems can be solved with a gas mixture in accordance with the invention in that the gas mixture further contains an inert, non-toxic trace gas.

The inert trace gas does not react with the other gases and can be present in a higher concentration than the desired concentration of NO. When NO and the trace gas are present in an exact and known ratio, the concentration of NO can be obtained by measuring the concentration of the trace gas in the mixture of the inventive gas mixture and breathing gas. The higher concentration of trace gas is easier to measure, and very good accuracy can be achieved. The concentration in the gas exhaled from the lungs can also be measured. If the trace gas is absorbed by the body, equilibrium for this intake must be awaited before the correct measurement values can be obtained when measurement is made of expired gas.

A refinement of the gas mixture is achieved in accordance with the invention wherein the inert, non-toxic gas also has limited solubility in water and fat.

A trace gas with limited solubility in water and fat is not absorbed by the body. Equilibrium develops when the lungs achieve the same concentration of trace gas as the concentration supplied, and the concentration of NO can be determined by measuring the concentration of trace gas in inspired gas or in expired gas.

One advantageous trace gas is a noble gas, preferably helium, He. Helium is inert and non-toxic. The gas mixture can therefore consist of NO and He alone. The addition of $N_2$ to this mixture is not necessary. $N_2$ is otherwise unsuitable as a trace gas, since it is present in the atmosphere.

Since noble gases are also present in well-known concentrations in the atmosphere, and thus in the breathing gas, measurement results must be corrected to compensate for this presence.

Another advantageous trace gas is $SF_6$. $SF_6$ is an inert gas which does not react with NO, has minimum solubility in water, is non-toxic and has a high hygienic limit value, 0.5%. Since $SF_6$ is not absorbed in the body, i.e., it does not pass the lung membrane, it can also be used in conjunction with measures to diagnose pulmonary function, i.e., determination of the lung's functional residual capacity (FRC). FRC can be determined when $SF_6$ is supplied to the lungs until equilibrium develops between the inspired and expired amounts of $SF_6$. The administration of $SF_6$ is then stopped, and the decline in $SF_6$ concentration in expired air is measured. FRC can then be calculated by determining the volume of $SF_6$ leaving the lungs. During treatment with NO, FRC can be measured between two different concentration levels of $SF_6$ in which the lower concentration consists of the therapeutic concentration of NO. In this way, the patient receives the requisite treatment at the same time as FRC is measured.

The concentration of $SF_6$ in the gas mixture is from 0.1% to 5%, preferably from 1% to 2%. However, the final mixture reaching the patient must never have an $SF_6$ content greater than the hygienic limit value.

An advantageous form of the gas mixture is obtained in accordance with the invention in that the mixture further contains a predetermined concentration of $N_2O$.

In contrast to NO, $N_2O$ is only absorbed to a limited degree depending on blood flow. When the body's intake of $N_2O$ is measured, the rate of blood flow through capillaries in the pulmonary alveoli can be determined.

Irrespective of the gas mixture's total composition of e.g. NO, $N_2$, He, $SF_6$, NO or other combinations, it is advantageous if the concentration of NO is from 10 to 100,000 ppm, preferably from 100 to 10,000 ppm. The concentration supplied to the patient is normally up to 100 ppm, depending on the purpose of the treatment.

A device for supplying a predetermined amount of NO to the lungs is achieved in accordance with the invention having a gas source containing a breathing gas, an inspiration tube, through which breathing gas and NO are fed into the lungs, and an expiration tube, through which breathing gas and NO are led out of the lungs, a second gas source for supplying the NO to the inspiration tube in the form of an inventive gas mixture as described above, and a gas concentration meter arranged in the gas flowways in order to measure the concentration of the trace gas.

By measuring the concentration of the trace gas, the concentration of NO is also obtained.

With this arrangement, the gas concentration meter can be calibrated after the equipment has been set up but before the patient is connected to the device by diverting the flows of breathing gas and gas mixture into the inspiration tube and the expiration tube. If an incorrect gas mixture is connected by mistake, e.g. a mixture with 10,000 ppm NO and 2% $SF_6$ instead of 1,000 ppm NO and 1% $SF_6$, the measurement error, even with a uncalibrated gas concentration meter, will be so large that it will be obvious to the operator that an incorrect gas mixture gas been connected.

Preferably, the gas concentration meter is arranged in the expiration tube in order to measure the concentration of the trace gas. Since the trace gas achieves equilibrium in the body or is not absorbed by the body at all, measurement (can be made of expired gas and still provide exact information on the concentration supplied. Moreover, the gas mixture can be delivered, in principle, directly to the lungs, since no meter is needed on the inspiratory side. The formation of $NO_2$ is hereby minimized. In a refinement of the device in accordance with the invention the device further has a flow meter in the expiration tube to measure the flow of expired gas and an analyzer to determine functional residual capacity, FRC, and the analyzer controls the second gas source so that it increases the amount of the inventive gas mixture added during a flushing-in phase from a first level to a second level until the trace gas attains equilibrium in the lungs. The analyzer also controls the second gas source so that, at the start of a flushing-out phase, it again adds gas mixture at the first level and, on the basis of gas concentration measurements made by the gas concentration meter and flow measurements made by the flow meter during the flushing-out phase of the elevated trace gas concentration, calculates FRC.

In this manner, any ongoing treatment with NO does not have to be terminated in order to calculate FRC. Instead, FRC is determined between two different levels of trace gas concentration.

Preferably, an additional gas concentration meter is arranged in the expiration tube in order to measure the concentration of NO.

Measurement of the trace gas makes the amount of supplied NO known, and NO intake in the body can be determined when the amount of NO exhaled is measured, thereby making possible a determination of the lung's diffusion capacity. In principle, the entire gas flow can be used for measuring the concentration of residual NO in the inventive method and device.

In conjunction with the delivery to the lungs of a gas mixture, which also contains a predetermined concentration of $N_2O$, it is preferable to arrange another additional gas concentration meter in the expiration tube to measure the concentration of $N_2O$. AS is the case with NO, this yields the concentration of inspired gas from measurement of the trace gas. Intake in the body can therefore be easily calculated.

A simultaneously filed and co-pending patent application having [attorney's docket no. P94, 156] Ser. No. 08/279,109 (Device for Supplying Breathing Gas to the Lungs of a Respiratory Subject, Olsson et al.) describes an apparatus which utilizes another principle for delivering e.g. NO to a lung. The apparatus disclosed in this co-pending application can also be used to supply the aforementioned inventive gas mixture.

An expiration valve can be arranged in the device of the expiration tube between the lungs of the respiratory subject and the gas concentration meter(s). The expiration valve regulates pressure in the expiration tube during both inspiration and expiration. Arrangement of the expiration valve in the expiration tube between the lungs and gas concentration meter(s) also permits the inspiratory flow to be fed undisturbed to the patient.

Preferably, a mixing container is arranged on the expiration tube between the expiration valve and the gas concentration meter(s).

Especially when slow gas concentration meters are used, measuring a floating average for the gas concentration, of a momentary value, is preferable. A corresponding average value for flow is preferably also determined at the same time. One minute is a suitable period for averaging. The mixing container is important in this instance, since it forms an average concentration for the gas passing through it. On the average, gas passes through the mixing container in a certain amount of time during which gases present for a longer period of time intermix, i.e., an average value for the average time through the container.

The problems in the formation of $NO_2$ have been mentioned above. Since this gas continuously forms at a specific reaction rate, determination of the NO concentration can be compensated for the formation of $NO_2$. If the concentration of $NO_2$ is measured on the expiratory side, the determination of the concentration of inspired NO and the diffusion of NO in the body can be compensated. A third possibility is to calibrate the entire system with a known gas mixture before the patient is connected to the device. Measurement of the $NO_2$ concentration can also be used to check for any leaks on the high-pressure side to ensure there is an influx of $O_2$ This monitoring can be connected to, e.g., an alarm.

DESCRIPTION OF THE DRAWINGS

The single figure is a schematic block diagram of an embodiment of a device for supplying breathing gas to the lungs of a respiratory subject, constructed in accordance with the principles of the present invention.

DESCRIPTION OF THE PREFERRED EMBODIMENTS

A device for delivering a predetermined concentration of NO to the lungs of a patient is generally designated 2 in the figure. The device 2 includes a ventilator unit 4 which controls and regulates operation of the entire device 2. Three gas connectors 6A, 6B and 6C are connected to a gas mixer 8 in the ventilator unit 4. The gases, in combination constituting a breathing gas for the patient, are fed to the ventilator unit 4 through the gas connectors 6A, 6B and 6C. These gases could be, e.g., oxygen and air, only two of the connectors 6A, 6B and 6C then being used. From the gas mixer 8, breathing gas passes via a first valve 10 at a predetermined pressure and flow to an inspiration tube 12. The inspiration tube 12 conducts the breathing gas to the patient's lungs. From a second gas mixer 14, a gas mixture containing a predetermined concentration of NO, $SF_6$ and $N_2O$, diluted with $N_2$ or He, can be fed to the inspiration tube 12 via a connecting tube 16. The ventilator unit 4 controls the gas mixture supplied via a control line 18. NO is strongly reactive and forms, with oxygen, $O_2$, nitrogen dioxide, $NO_2$, a toxic gas. The gas mixture from the second gas mixer 14 should therefore be added as close to the patient as possible to minimize the concentration of $NO_2$ and to ensure that the desired concentration of NO is delivered to the lungs. The gas mixture may contain, e.g., 0.1% NO, 2% $SF_6$, 1% $N_2O$, $N_2$ or He comprises the remainder.

Gas exhaled by the patient passes through an expiration tube 20 back to the ventilator unit 4. This expired gas is then conducted away via a second valve 22 to evacuation, e.g. into ambient air or collection vessels for expired gas. A positive end expiratory pressure (PEEP), for example, can be maintained with the second valve 22.

In the expiration tube 20, after the second valve 22, a first gas meter 24 is disposed which measures the concentration of $EF_6$ in the expired gas and which sends a measurement signal, via a first signal line 26, to the ventilator unit 4. A second gas meter 28 is also disposed in the expiration tube 20 after the second valve 22, which measures the concentration of NO in expired gas and which sends a measurement signal, via a second signal line 30, to the ventilator unit 4. A third gas meter 32 is also disposed in the expiration line 20 after the second valve 22, which measures the concentration of $N_2O$ in the expired gas and which sends a measurement signal, via signal line 34, to the ventilator unit 4.

A mixing container 40 is arranged between the gas meters 24, 28 and 32 and the second valve 22. The mixing container 40 makes possible collection and mixing of gas over a long period of time, thereby forming an average value for the concentration of NO, $N_2O$ and $N_2$. $SF_6$ is unaffected.

The addition of NO via the second gas mixer 14 can be performed for diagnostic or therapeutic reasons, e.g. for determining the diffusion capacity of the lung or for reducing the resistance to blood perfusion in the pulmonary alveoli. The known ratio between the concentration of NO and $SF_6$ in the gas mixture from the second mixer 14 permits determination of the amount of NO delivered to the patient by measurement of the concentration of $SF_6$ in the expiration tube 20. $SF_6$ is an inert gas which is not absorbed in the body, and equilibrium develops between inspired and expired $SF_6$ after a small number of respiratory cycles. If the concentration of NO in the mixed inspiratory gas changes, the concentration of $SF_6$ also changes, and a new equilibrium concentration will develop in the lungs, as measured in the expired gas. In this manner, the amount of NO supplied can be determined exactly. Compensation for the $NO_2$ which still forms can be made in any of the ways described above.

The concentration of trace gas can also be measured in the inspiration tube. The equilibrium concentration of the lungs' content of trace gas will then not affect the measurement, and all changes are recorded immediately. Measurement on the expiratory side also has other advantages. The inspiratory flow can pass undisturbed to the lungs. The gas mixture can be added even closer to the lungs, in principle inside the lungs, thereby minimizing reactions between NO and $NO_2$. Breathing gas and the gas mixture also have time to mix thoroughly before measurement takes place, which is otherwise difficult to achieve on the inspiratory side because of the necessity of mixing the gases very close to the lungs.

When the concentration of NO the in expired gas is measured, the amount of NO absorbed by the body can be determined. In this way, the diffusion capacity of the lungs can be determined, since NO molecules can, in principle, be absorbed by blood in unlimited amounts, so no counterpressure builds up to limit diffusion of NO into the blood.

If $N_2O$, whose concentration is obtained in the same way as the determination of NO, i.e., through measurement of the concentration of $SF_6$, is added and the $N_2O$ content of expired gas is measured, the flow of blood through the lungs can be determined. This is because $N_2O$ molecules, in contrast to NO molecules, can only be absorbed into blood to a limited degree. The intake of $N_2O$ molecules is therefore a measure of blood perfusion through the lungs. $N_2O$ can be advantageously added in two different concentrations, and the change in the concentration of $N_2O$ in expired gas can then be measured to determine the flow of blood through the lungs.

The device 2 also includes an analyzer 36 for determining functional residual capacity, FRC. The analyzer 36 can control the second gas source 14 and receive measurement values from the gas concentration meters 24, 28 and 32 and from a flow meter 38 which measures the flow of the expired gas. When the flow from the second gas source 14 is increased for a given period of time, a new equilibrium develops for the $SF_6$ concentration in the lungs. When the flow from the second gas source 14 is restored, the lungs will gradually be purged of surplus $SF_6$. The analyzer can calculate the volume of this surplus on the basis of concentration values and flow values measured in the time required to flush surplus $SF_6$ out of the lungs. The calculated volume is then used for determining FRC.

It was noted above that only two of the three gas connectors 6A, 6B or 6C are used when air and $O_2$ serve as the breathing gas. In certain situations, the addition of gas mixture through the third gas connector 6C may then be appropriate instead of having a separate connector in the inspiration tube 12. The first valve 10 can be replaced with three valves, respectively controlling the flow of gas from the three gas connectors 6A, 6B and 6C. In this version, a Servo Ventilator 300 commercially available from Siemens-Eiema, Sweden, can be advantageously used.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for administering a predetermined amount of NO to a patient's lungs comprising:

a first gas source containing a breathing gas;

a second gas source containing a gas mixture having a predetermined concentration of NO and a predetermined concentration of an inert, nontoxic trace gas so that said trace gas and said NO are present in said gas mixture in a predetermined ratio;

an inspiration tube connected to said first and second gas sources and adapted to deliver said breathing gas and said gas mixture to the lungs of said respirating subject;

an expiration tube adapted to conduct expired breathing gas and NO from the lungs of said respirating subject, said inspiration tube and said expiration tube in combination comprising gas flowways; and gas concentration meter means, disposed in said gas flowways, for measuring the concentration of said trace gas for obtaining, from said ratio, the concentration of said NO.

2. A device as claimed in claim 1 wherein said gas concentration meter means is disposed in said expiration tube.

3. A device as claimed in claim 1 further comprising:

a flow meter disposed in said expiration tube which measures a flow of expired gas from a respirating subject; and analyzer means for controlling said second gas source for increasing, during a flushing-in phase, an amount of said gas mixture from a first level to a second level at which said trace gas attains equilibrium in the lungs of said respirating subject, and for controlling said second gas source, at a start of a flushing-out phase, for adding said gas mixture at said first level and for calculating, during said flushing-out phase, the functional residual capacity of the lungs of said respiration subject dependent on said concentration of said trace gas measured by said gas concentration meter and said flow of expired gas measured by said flow meter.

4. A device as claimed in claim 1 further comprising a further gas concentration meter means disposed in said expiration tube for measuring the concentration of NO.

5. A device as claimed in claim 4 wherein said second gas source is connected for adding said gas mixture to said inspiration tube, and further comprising a further gas concentration meter means disposed in said expiration tube for measuring a concentration of $N_2O$.

6. A device as claimed in claim 1 further comprising an expiration valve disposed in said expiration tube between a patient's lungs and said gas concentration meter means.

7. A device as claimed in claim 6 further comprising a mixing container disposed in said expiration tube between said expiration valve and said gas concentration meter means.

* * * * *